(12) United States Patent
Partlett et al.

(10) Patent No.: US 8,690,871 B2
(45) Date of Patent: Apr. 8, 2014

(54) CATHETER HANDLE AND A CATHETER ASSEMBLY INCLUDING SUCH A HANDLE

(75) Inventors: Matthew Partlett, Allawah (AU); Zoran Milijasevic, Bayview (AU); Neil Lawrence Anderson, Roseville (AU)

(73) Assignee: Cathrx Ltd., Homebush Bay (AU)

(\*) Notice: Subject to any disclaimer, the term of this patent is extended or adjusted under 35 U.S.C. 154(b) by 854 days.

(21) Appl. No.: 11/885,024

(22) PCT Filed: Mar. 1, 2006

(86) PCT No.: PCT/AU2006/000266
§ 371 (c)(1),
(2), (4) Date: Jul. 9, 2008

(87) PCT Pub. No.: WO2006/092014
PCT Pub. Date: Sep. 8, 2006

(65) Prior Publication Data
US 2008/0275388 A1    Nov. 6, 2008

Related U.S. Application Data

(60) Provisional application No. 60/659,020, filed on Mar. 4, 2005.

(51) Int. Cl.
*A61B 18/14* (2006.01)
(52) U.S. Cl.
USPC .......... 606/41; 606/48; 606/49; 606/50; 607/101; 607/102; 604/95.04; 604/95.05
(58) Field of Classification Search
CPC ...... A61B 18/08; A61B 18/082; A61B 18/12; A61B 18/14; A61B 18/1402; A61B 18/1492; A61B 2018/0091; A61B 2018/1495; A61B 2017/0046; A61B 2017/2841; A61B 2017/2924
USPC ................ 606/41, 48–50; 607/101–102; 604/95.04–95.05; D24/133
See application file for complete search history.

(56) References Cited

U.S. PATENT DOCUMENTS

| 3,539,034 A | | 11/1970 | Tafeen |
| 4,718,419 A | | 1/1988 | Okada |
| 4,763,647 A | | 8/1988 | Gambale |
| 4,960,134 A | \* | 10/1990 | Webster, Jr. .................. 607/116 |
| 5,125,896 A | \* | 6/1992 | Hojeibane .................. 604/95.04 |

(Continued)

FOREIGN PATENT DOCUMENTS

| DE | 36 26 371 | 2/1987 |
| EP | 0 132 344 A2 | 1/1985 |

(Continued)

OTHER PUBLICATIONS

Supplementary European Search Report completed Jun. 7, 2010, for European Patent Application No. 06 70 4940, six pages.

(Continued)

*Primary Examiner* — Linda Dvorak
*Assistant Examiner* — Khadijeh Vahdat
(74) *Attorney, Agent, or Firm* — TraskBritt

(57) ABSTRACT

A catheter handle includes a handle body. A steering control mechanism is displaceably carried on the handle body. An electrode sheath carrier is carried on the handle body, the electrode sheath carrier being displaceable at least relative to the steering control mechanism.

28 Claims, 7 Drawing Sheets

(56) References Cited

U.S. PATENT DOCUMENTS

| | | | |
|---|---|---|---|
| 5,190,050 A * | 3/1993 | Nitzsche | 600/585 |
| 5,275,151 A | 1/1994 | Shockey et al. | |
| 5,306,245 A | 4/1994 | Heaven | |
| 5,358,479 A * | 10/1994 | Wilson | 604/95.04 |
| 5,364,352 A | 11/1994 | Cimino et al. | |
| 5,395,329 A | 3/1995 | Fleischhacker et al. | |
| 5,441,483 A | 8/1995 | Avitall et al. | |
| 5,454,787 A | 10/1995 | Lundquist et al. | |
| 5,478,330 A * | 12/1995 | Imran et al. | 604/526 |
| 5,545,200 A * | 8/1996 | West et al. | 607/122 |
| 5,607,392 A | 3/1997 | Kanner et al. | |
| 5,662,606 A | 9/1997 | Cimino et al. | |
| 5,826,576 A * | 10/1998 | West | 600/373 |
| 5,843,103 A | 12/1998 | Wulfman | |
| 5,861,024 A * | 1/1999 | Rashidi | 607/122 |
| 5,882,333 A | 3/1999 | Schaer et al. | |
| 5,906,627 A | 5/1999 | Spaulding et al. | |
| 5,938,694 A | 8/1999 | Jaraczewski et al. | |
| 6,048,339 A | 4/2000 | Zirps et al. | |
| 6,083,222 A * | 7/2000 | Klein et al. | 606/41 |
| 6,413,234 B1 | 7/2002 | Thompson et al. | |
| 6,551,302 B1 * | 4/2003 | Rosinko et al. | 604/505 |
| 6,666,864 B2 | 12/2003 | Bencini et al. | |
| 7,354,437 B2 * | 4/2008 | Shin et al. | 606/41 |
| 2001/0007070 A1 | 7/2001 | Stewart et al. | |
| 2001/0014770 A1 | 8/2001 | Olson et al. | |
| 2002/0019630 A1 | 2/2002 | Falwell et al. | |
| 2002/0077590 A1 | 6/2002 | Ponzi et al. | |
| 2002/0082594 A1 | 6/2002 | Hata et al. | |
| 2003/0014037 A1 * | 1/2003 | Thompson et al. | 604/528 |
| 2003/0069570 A1 * | 4/2003 | Witzel et al. | 606/28 |
| 2003/0109778 A1 | 6/2003 | Rashidi | |
| 2003/0187389 A1 | 10/2003 | Morency et al. | |
| 2003/0208198 A1 | 11/2003 | Hayzelden et al. | |
| 2003/0220676 A1 * | 11/2003 | Helland | 607/122 |
| 2004/0039338 A1 * | 2/2004 | Lee et al. | 604/164.12 |
| 2004/0116849 A1 * | 6/2004 | Gardeski | 604/95.04 |
| 2004/0225256 A1 * | 11/2004 | Ponzi et al. | 604/95.04 |
| 2005/0004515 A1 | 1/2005 | Hart et al. | |
| 2006/0084964 A1 | 4/2006 | Knudson et al. | |
| 2006/0184105 A1 | 8/2006 | Townsend et al. | |
| 2006/0224111 A1 | 10/2006 | Rosenman et al. | |
| 2008/0045921 A1 * | 2/2008 | Anderson et al. | 604/508 |
| 2010/0137955 A1 | 6/2010 | Milijasevic et al. | |
| 2010/0331776 A1 | 12/2010 | Salahieh et al. | |

FOREIGN PATENT DOCUMENTS

| | | |
|---|---|---|
| EP | 0 132 344 A3 | 1/1985 |
| EP | 1 709 987 | 10/2006 |
| JP | 62-243566 A | 10/1987 |
| JP | H04-319365 | 11/1992 |
| JP | 6-232944 A | 8/1994 |
| JP | H07-255855 | 10/1995 |
| JP | 9-135905 A | 5/1997 |
| JP | 9-285546 A | 11/1997 |
| JP | 10-500334 T | 1/1998 |
| JP | 11-401 A | 1/1999 |
| JP | 2001-502186 T | 2/2001 |
| JP | 2001-505076 | 4/2001 |
| JP | 2001-513692 T | 9/2001 |
| JP | 7-88093 A | 4/2005 |
| WO | WO 94/11057 | 5/1994 |
| WO | WO-95/31243 A1 | 11/1995 |
| WO | WO-96/37252 A1 | 11/1996 |
| WO | WO 98/06337 | 2/1998 |
| WO | WO-98/38926 A1 | 9/1998 |
| WO | WO 03/090833 | 11/2003 |
| WO | WO 2005/094661 | 10/2005 |
| WO | WO-2006/012668 A1 | 2/2006 |

OTHER PUBLICATIONS

Japanese Office Action mailed on Jun. 29, 2010, for Japanese Patent Application No. 2007-557282, filed on Mar. 1, 2006, four pages.

International Search Report mailed on May 9, 2006, for PCT Application No. PCT/AU2006/000266 filed Mar. 1, 2006, five pages.

Human Genome Expression Profiles, Adipose Tissue Liposarcoma, available at lutolitelethon.bio.unipd.it/bioinfo/HGXP 170/Tissues/adipose t 1ib886.hunl (last visited Jun. 2, 2011) p. 1.

Human Genome Expression Profiles, Ovary Papillary Serous Carcinoma, available at htto://telethon.bio.unipd.it/bioinfo/HGXP 170f Fissues/ovary t 1ib510.html (last visited Jun. 2, 2011) pp. 1-18.

Schoch et al. "Acute Myeloid Lukemias with Ceciprocal Rearrangements can Be Distinguished by Specific Gene Expression Profiles", PNAS, Jul. 23, 2002, vol. 99, No. 15, pp. 10,008-10,013.

Kolhmann et al. "Molecular Characterization of Acute Leukemias by Use of Microarray Technology." Genes, Chromosomes, & Cancer, Jan. 9, 2003, vol. 37, pp. 396-405.

Affymetrix Microarray Brands, http://www.affymetrix.com/estore/, 2009, pp. 1-2.

UniGene Entry Hs.356623 Has Been Retired, NCBI, Feb. 8, 2011, pp. 1-2.

UniGene Entry HS.454253 Has Been Retired, NCBI, Feb. 1, 2011, p. 1.

Golub et al. "Molecular Classification of Cancer: Class Discovery and Class Prediction by Gene Expression Monitoring." Science, New Series, vol. 286, No. 5439, Oct. 15, 1999, pp. 531-537.

\* cited by examiner

CATHETER HANDLE AND A CATHETER ASSEMBLY INCLUDING SUCH A HANDLE

CROSS-REFERENCE TO RELATED APPLICATIONS

This application is a national phase entry under 35 U.S.C. §371 of International Application No. PCT/AU2006/000266, filed on Mar. 1, 2006, published in English as International Patent Publication WO 2006/092014 A1 on Sep. 8, 2006, which claims the benefit of U.S. Provisional Application No. 60/659,020, filed on Mar. 4, 2005, the disclosures of which are incorporated herein by reference in their entirety.

TECHNICAL FIELD

This invention relates, generally, to catheters and, more particularly, to a catheter handle and to a catheter assembly including the handle.

BACKGROUND

Catheters are increasingly being used to perform various functions in diagnosis and treatment of patients. Often, the catheter is inserted into a patient's body via the patient's vascular system and is steered to the desired position.

It will be appreciated that the steering of the catheter involves careful manipulation in order not to damage the vascular system. As a consequence of this, a steering mechanism incorporated in the catheter generally provides for reasonably large radii of curvature.

Also, in the positioning of devices, both for sensing signals and for heat treatment, the shape of the device when deflected sometimes makes accessing a particular part of the body difficult, for example, a catheter to be placed in the coronary sinus of the heart.

In addition, a site to be treated using the catheter more often than not has surface irregularities that must be overcome in order to obtain, for example, suitable electrode-tissue contact.

BRIEF SUMMARY OF THE INVENTION

According to a first aspect of the invention, there is provided a catheter handle that includes:
 a handle body;
 a steering control mechanism displaceably carried on the handle body; and
 an electrode sheath carrier carried on the handle body, the electrode sheath carrier being displaceable at least relative to the steering control mechanism.

The handle body may be an elongate tubular member having a proximal end and a distal end, an electrical connector being arranged at, or adjacent, the proximal end of the handle body.

Conveniently, the steering control mechanism may comprise a displaceable unit carried on the handle body. The displaceable unit may comprise a cylindrical element fast with a slider received within the handle body.

To facilitate displacement of the steering control mechanism relative to the handle body, the steering control mechanism may carry a manipulating element. The manipulating element may be a flange extending radially outwardly from the cylindrical element of the steering control mechanism.

The handle body and the slider may include complementary guide formations for guiding displacement of the steering control mechanism relative to the handle body. The complementary guide formations may include at least one guide formation defined by the handle body with the slider defining at least one guide element received in the guide formation. Preferably, the guide formation of the handle body comprises a pair of diametrically opposed, longitudinally extending guide slots with the slider having a pair of radially outwardly extending guide elements received in the slots. Thus, the steering control mechanism may be at least longitudinally displaceable relative to the handle body.

The electrode sheath carrier may comprise a sleeve that cooperates with the cylindrical element of the steering control mechanism. The sleeve may carry an electrode connector for electrical connection to electrodes of an electrode sheath connectable to the carrier. Preferably, the connector carries a retaining formation for retaining the electrode sheath relative to the sleeve.

The sleeve and the steering control mechanism may include complementary cooperating formations for controlling displacement of the sleeve relative to the cylindrical element of the steering control mechanism. The cooperating formations may comprise at least one axially extending slot in a wall of one of the cylindrical elements and the sleeve and a follower formation carried by the other of the cylindrical elements and the sleeve for limiting displacement of the sleeve and the cylindrical elements relative to each other.

Once again, to inhibit the ingress of foreign matter into the interior of the handle body, a sealing arrangement may be arranged between the cylindrical element and the sleeve at each end of the slot.

At least one of the handle body and the steering control mechanism may include anchoring formations for anchoring a steering shaft used in a catheter attached to the handle. Preferably, both the handle body and the steering shaft include anchoring formations, the anchoring formations each being associated with different parts of the steering shaft. An anchoring formation of the handle body may comprise a boss arranged within the handle body. The boss may have an axially extending passage defined therein in which a first part of the steering shaft is receivable, the first part of the steering shaft being retained in position in use via a securing element. The slider of the steering control mechanism may define the anchoring formation in which a second part of the steering shaft is receivable, the second part of the steering shaft being retained in position in use via a securing element. The securing elements for both the slider of the steering control mechanism and the boss of the handle body may be in the form of grub screws received in radially extending bores in each of the slider and the boss of the handle body.

According to a second aspect of the invention, there is provided a catheter assembly that includes:
 a catheter handle having a handle body, a steering control mechanism displaceably arranged relative to the handle body and an electrode sheath carrier displaceably arranged relative to the steering control mechanism and the handle body;
 a steering shaft connected at least to the steering control mechanism; and
 an electrode sheath carried by the electrode sheath carrier.

The steering shaft may be releasably connected at least to the steering control mechanism. Preferably, the steering shaft is releasably connected both to the steering control mechanism and to the handle body so that relative displacement between the steering control mechanism and the handle body effects steering of a distal region of the steering shaft and, consequently, an electrode sheath of the catheter received over the steering shaft.

The steering shaft used with the catheter handle may be of the type described in the Applicant's co-pending International Application No. PCT/AU2005/000216 dated 18 Feb. 2005 entitled "A steerable catheter." The contents of that International application are incorporated in this specification by reference.

Thus, the steering shaft may include a tubular member having a bend-enhancing region and in which an actuator may be slidably received, the actuator and the tubular member being attached to each other distally, a proximal end of one of the tubular member and the actuator being connected to the steering control mechanism and a proximal end of the other of the tubular member and the actuator being connected to the handle body. To facilitate modularity, the parts of the steering shaft may be releasably connectable to their respective components of the handle body.

A distal region of the steering shaft may include a plurality of contact-enhancing regions for urging an electrode into contact with tissue at a site being treated by appropriate manipulation of the steering shaft relative to the electrode sheath, the electrode sheath carrying a plurality of spaced electrodes. The contact-enhancing regions of the steering shaft may be arranged distally of the distal attachment of the actuator and the tubular member. Preferably, the contact-enhancing regions form part of a distal region of the actuator of the steering shaft.

The electrode sheath carrier may be displaceably carried relative to the steering control mechanism. In an embodiment, the electrode sheath carrier may be displaceably carried on the steering control mechanism. Further, the electrode sheath carrier and the steering control mechanism may be relatively displaceable in an axial direction and rotationally with respect to each other.

According to a third aspect of the invention, there is provided a method of controlling operation of a catheter, the method including:
  axially displacing an electrode sheath relative to a steering shaft received in a lumen of the electrode sheath so that a distal portion of the electrode sheath is unsupported by a distal end of the steering shaft; and
  allowing flexing of the unsupported distal portion of the electrode sheath relative to the distal end of the steering shaft.

The method may include rotating the electrode sheath relative to the steering shaft to effect rotation of the flexed part of the electrode sheath through a predetermined arc.

According to a fourth aspect of the invention, there is provided a catheter stylet that includes:
  an elongate element having a proximal end and a distal end; and
  a plurality of spaced contact-enhancing regions arranged at the distal end of the elongate element.

The contact-enhancing regions may serve to urge an electrode into contact with tissue at a site being treated by appropriate manipulation of the stylet relative to an electrode sheath, carrying a plurality of electrodes, in a lumen of which the stylet is receivable, in use.

The contact-enhancing regions may be in the form of a series of undulations having a "wavelength" approximating that of a centre-to-centre distance of each electrode of the electrode sheath.

Conveniently, the stylet may be implemented as an actuator of a catheter steering shaft. Thus, by displacing the electrode sheath relative to the contact-enhancing regions of the stylet, improved electrode-tissue contact or easier accessibility to a particular bodily location may be able to be obtained. It will be appreciated that the contact-enhancing regions are arranged distally of an attachment point of the actuator to the tubular member of the steering shaft.

DETAILED DESCRIPTION OF THE INVENTION

Figure 1:
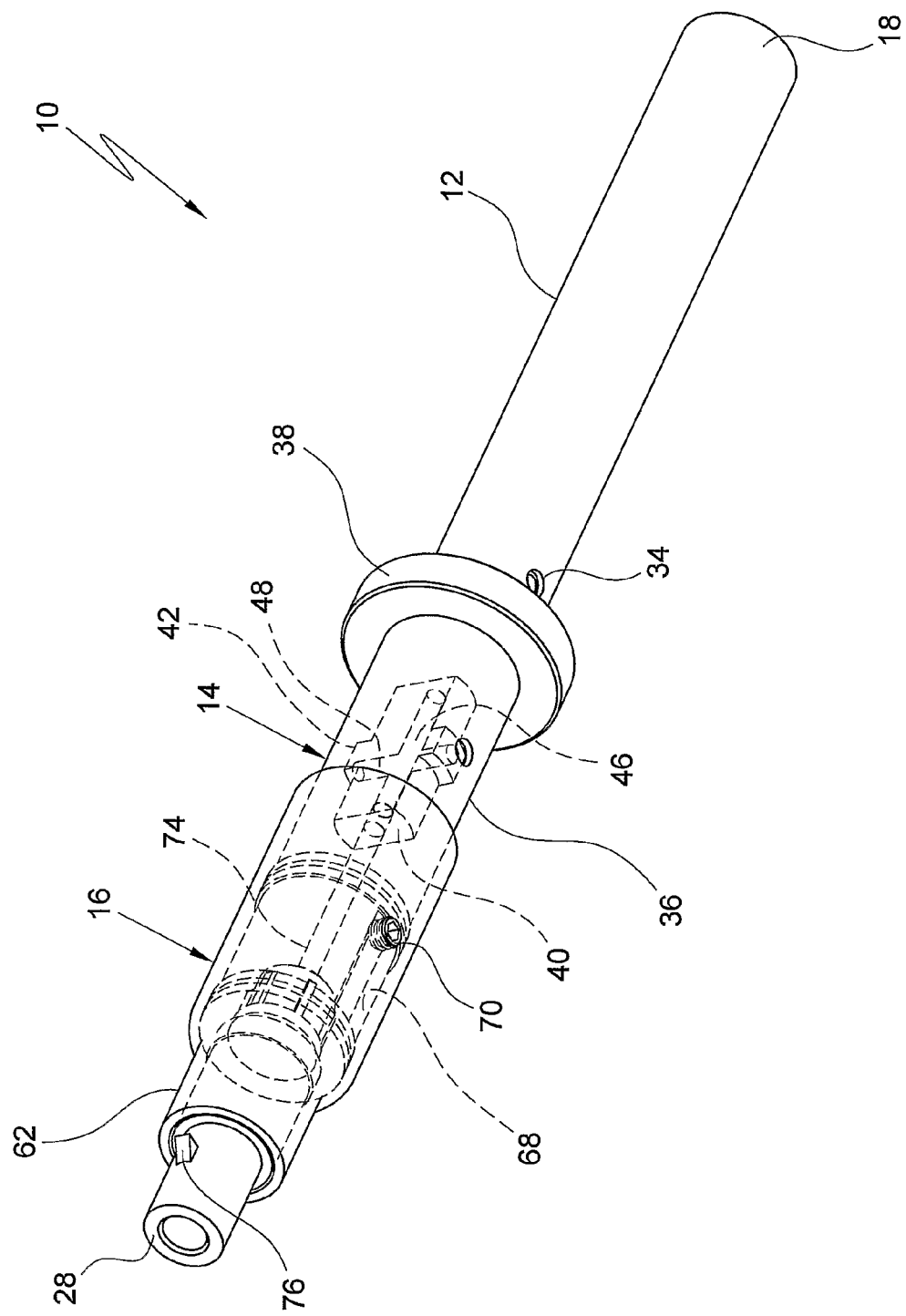
FIG. 1 shows a three-dimensional view of a catheter handle, in accordance with an embodiment of the invention, in a first position.

Referring initially to FIGS. 1 to 6 of the drawings, a catheter handle, in accordance with an embodiment of the invention, is designated generally by the reference numeral 10.

The handle includes a handle body 12, a steering control mechanism 14 displaceably carried on the handle body 12 and an electrode sheath carrier 16 displaceably carried relative to the steering control mechanism 14.

Figure 4:
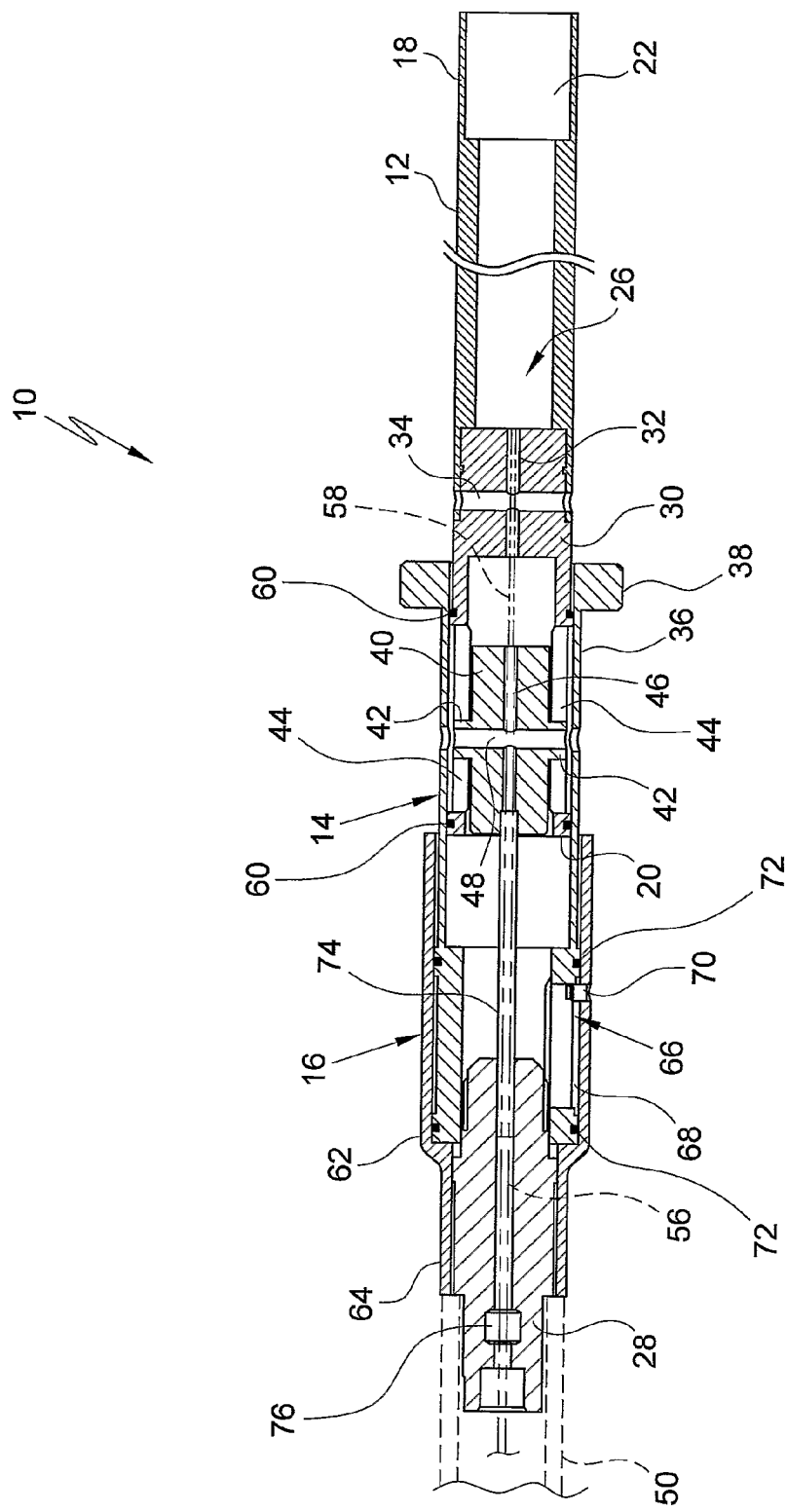
FIG. 4 shows a cross-sectional side view of the catheter handle in the first position.

As shown in greater detail in FIG. 4 of the drawings, the handle body 12 has a proximal end 18 and a distal end 20. An electrical connector 22 is housed in the proximal end 18 of the handle body 12 for connection to a patient cable of an electrical control unit (not shown) and via which electrodes of a catheter 24 (FIGS. 7A and 7B) are controlled.

The handle body 12 has a passage 26 extending through it through which leads (not shown) from the connector 22 to a connector 28 extend. The connector 28 forms part of the sheath carrier 16, the connector 28 protruding from a distal end of the sheath carrier 16.

A boss 30 is arranged in the passage 26, proximally of the distal end 20 of the handle body 12. The boss 30 has a passage 32 extending axially therethrough. A pair of transversely extending bores 34 are defined in the boss 30 intersecting the passage 32.

The steering control mechanism 14 includes a displaceable unit in the form of a cylindrical element 36 slidably mounted over the distal end 20 of the handle body 12. A manipulating element in the form of a radially outwardly extending flange 38 is arranged at a proximal end of the cylindrical element 36.

The cylindrical element has a slider 40 fast with it. The slider 40 is received in the passage 26 of the handle body 12 and slides axially together with the cylindrical element 36. The slider 40 has guide elements in the form of diametrically opposed tabs 42 projecting radially outwardly. The tabs 42 are received in a pair of diametrically opposed, axially extending slots 44 defined in the handle body 12. The tabs 42 received in the slots 44 control axial displacement of the steering control mechanism 14 relative to the handle body 12.

The slider 40 has an axial passage 46 extending through it. A pair of transversely extending bores 48 intersect the passage 46. The slider 40 is oblong in cross-sectional shape allowing the passage of leads from the connector 22 to the connector 28 past sides of the slider 40. The boss 30 is of a similar construction.

Figure 7A:
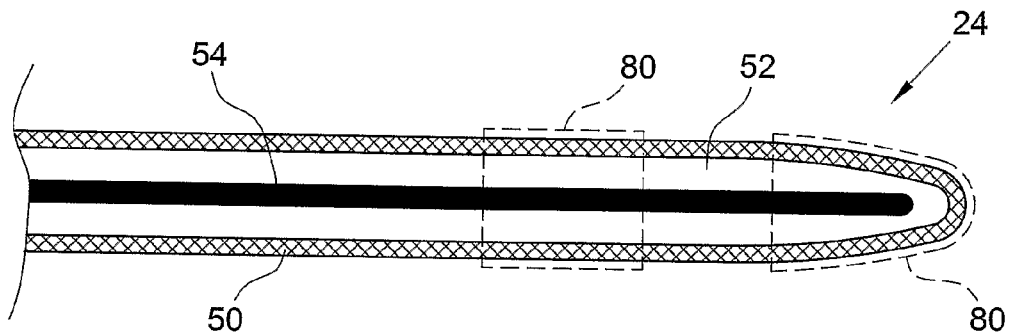
FIG. 7A shows a schematic illustration of a distal part of a catheter forming part of a catheter assembly, in accordance with another embodiment of the invention, with the catheter handle of the assembly being in its first position.
Figure 7B:
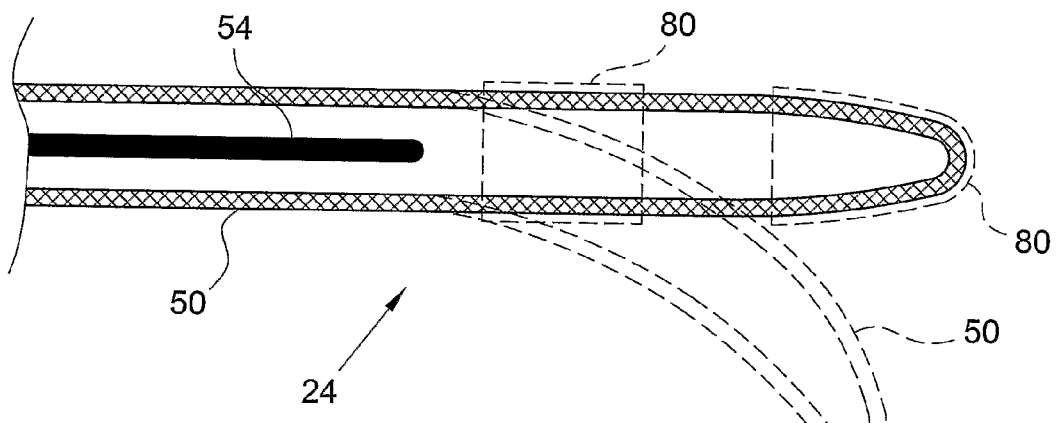
FIG. 7B shows a schematic illustration of the distal part of the catheter when the catheter handle is in its second position.

The catheter 24 includes an electrode sheath 50 defining a lumen 52 (FIG. 7A). A steering shaft 54 is received in the lumen 52 of the catheter 24. As indicated above, the steering shaft 54 is of the type described in the Applicant's co-pending International Application No. PCT/AU2005/000216. The steering shaft 54 is, therefore, of the type having an elongate tubular member, shown schematically at 56 in FIG. 4 of the drawings, in which a solid or hollow wire actuator, shown schematically at 58 in FIG. 4 of the drawings, is received. The distal end of the actuator 58 is fast with a distal region of the tubular member 56 (as shown at 104 in FIG. 9 of the drawings). Relative displacement between the tubular member 56 and the actuator 58 effects steering of a distal end of the steering shaft 54. The tubular member 56 is, therefore, held captive, in use, in the passage 46 of the slider 40 by a grub screw (not shown) received in each of the bores 48. Similarly, the actuator 58 is held captive in the passage 32 of the boss 30 of the handle body 12 by grub screws (also not shown) received in each of the bores 34 of the boss 30. By slidably displacing the steering control mechanism 14 axially relative to the handle body 12, axial displacement of the tubular member 56 of the steering shaft 54 relative to the actuator 58 occurs to effect steering of the distal end of the steering shaft 54 and, accordingly, the distal end of the catheter 24.

To inhibit the ingress of foreign material into the handle body 12, sealing formations in the form of O-rings 60 are received in seats defined at opposed ends of the slots 44.

The electrode sheath carrier 16 includes a sleeve 62 mounted over a distal portion of the cylindrical element 36 of the steering control mechanism 14. The sleeve 62 has a waisted distal region 64 in which the connector 28 is secured.

The sleeve 62 and the cylindrical element 36 of the steering control mechanism 14 have complementary cooperating formations 66 for controlling displacement of the sleeve 62 relative to the steering control mechanism 14. The cooperating formations 66 are in the form of an axially extending slot 68 defined in a wall of the cylindrical element 36 of the steering control mechanism 14 and a follower 70 protruding radially inwardly from a wall of the sleeve 62. To facilitate assembly of the catheter handle 10, the follower 70 is, conveniently, a removable grub screw.

Once again, to inhibit the ingress of foreign material into the interior of the handle 10, a pair of seats is defined at opposite ends of the slot 68 in each of which a seal in the form of an O-ring 72 is received.

A guide tube 74 projects from the distal end 20 of the handle body 12 in which the steering shaft 54 is received and is supported.

The electrode sheath 50 of the catheter 24 is releasably connected to the connector 28 of the sheath carrier 16 by means of clips 76.

In certain circumstances, it may be desirable to have rotational displacement of the electrode sheath 50 relative to the steering shaft 54. Therefore, in FIG. 6, another embodiment of the handle 10 is shown. In this embodiment, in addition to the axially extending slot 68 of the complementary cooperating formations 66, a plurality of longitudinally spaced, transversely extending slots 78 are also defined. This allows the electrode sheath 54 to be rotated through a predetermined arc relative to the steering shaft 54, possibly after axial displacement of the sleeve 62 of the electrode sheath carrier 16 relative to the cylindrical element 36 of the steering control mechanism 14 has occurred.

In use, the steering shaft 54 is releasably coupled to the handle 10 by securing the tubular member 56 of the steering shaft 54 to the slider 40 of the steering control mechanism 14 and the actuator 58 to the boss 30 of the handle body 12. The tubular member 56 of the steering shaft 54 is secured to the slider 40 by inserting grub screws into the bores 48 of the slider 40. Likewise, the actuator 58 is secured in position relative to the boss 30 by inserting grub screws into the bores 34 in the boss 30. An electrode sheath of the catheter 24 is clipped into position on the distal end of the connector 28 over the steering shaft 54.

The catheter 24 is inserted into an introducer (not shown) and the introducer is inserted into the vascular system of a patient. The introducer delivers the distal end of the catheter 24 to the desired site in the patient's body, for example, in an atrium of a heart of the patient. At the site, the distal end of the catheter 24 is urged through the distal end of the introducer. This exposes electrodes 80 carried by the distal end of the electrode sheath 50 of the catheter 24. The electrodes 80 are able to be used for ablating tissue to create lesions in the tissue, for example, in the treatment of heart arrhythmias. It also frees up a bend-enhancing region 106 (FIG. 9) of the tubular member 56 of the steering shaft 54. By relative axial displacement between the tubular member 56 and the actuator 58 of the steering shaft 54, bending of the steering shaft 54 at the bend-enhancing region 106 is achieved allowing the catheter 24 to be steered through the vascular system of the patient.

It will be appreciated that the steering shaft 54, being of wire has a predetermined radius of curvature. This may, in certain circumstances, inhibit adequate electrode-tissue contact to effect ablation of the tissue or access to particular parts of the site in the patient's body. In other words, greater flexibility of the electrode sheath 50 may be required.

Figure 2:
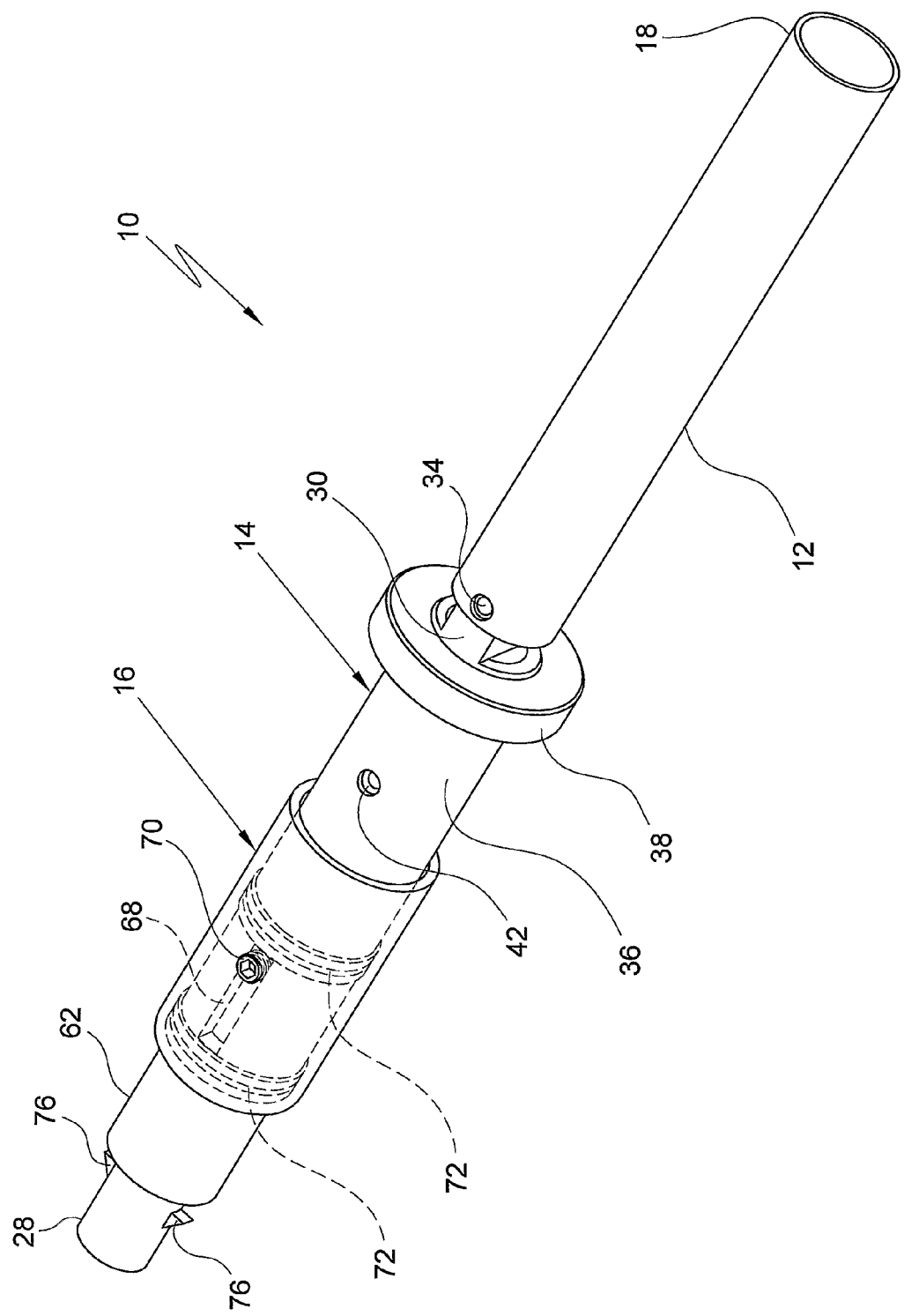
FIG. 2 shows a further three-dimensional view of the catheter handle in the first position.
Figure 3:
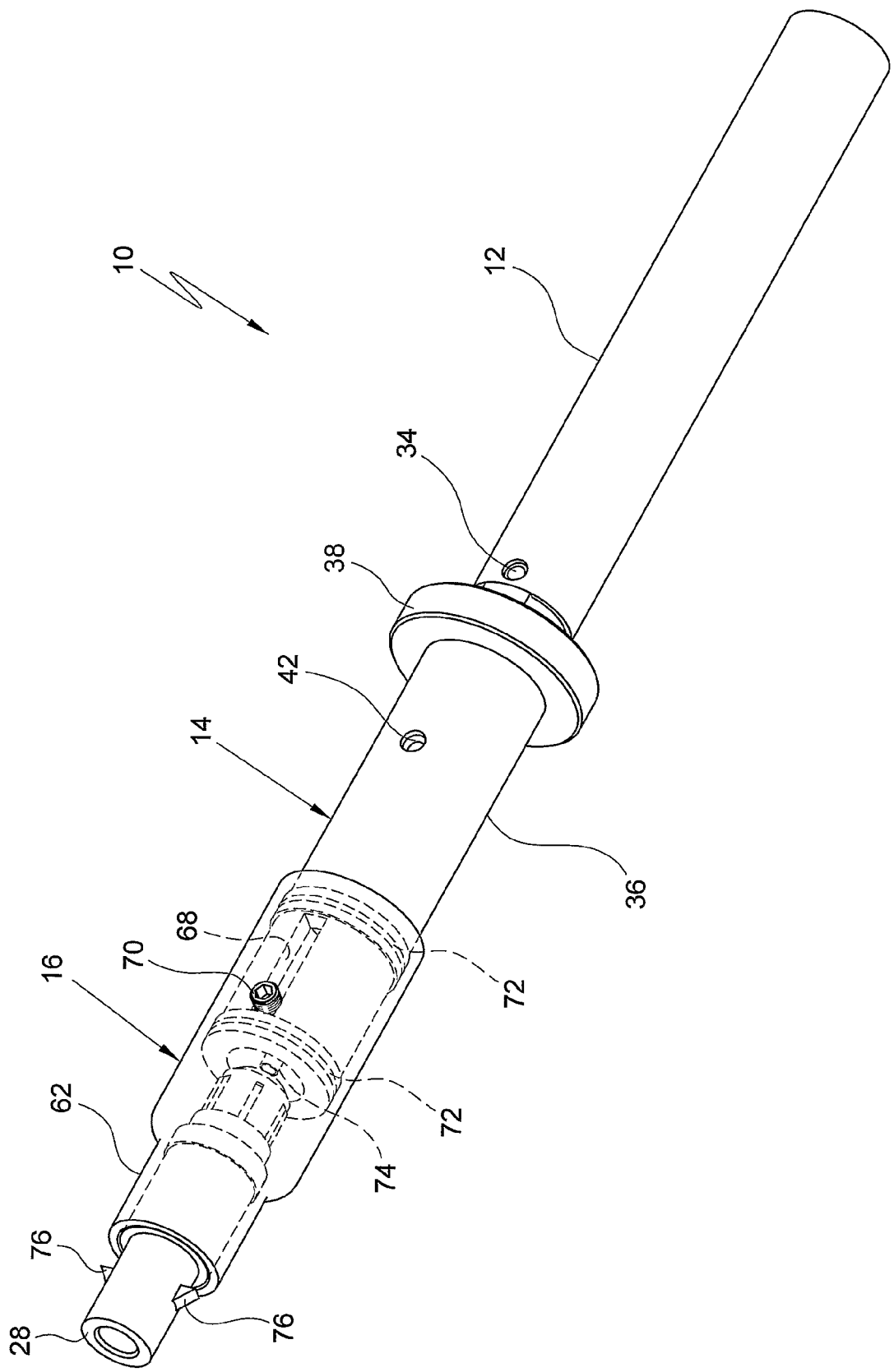
FIG. 3 shows a three-dimensional view of the catheter handle in a second position.
Figure 5:
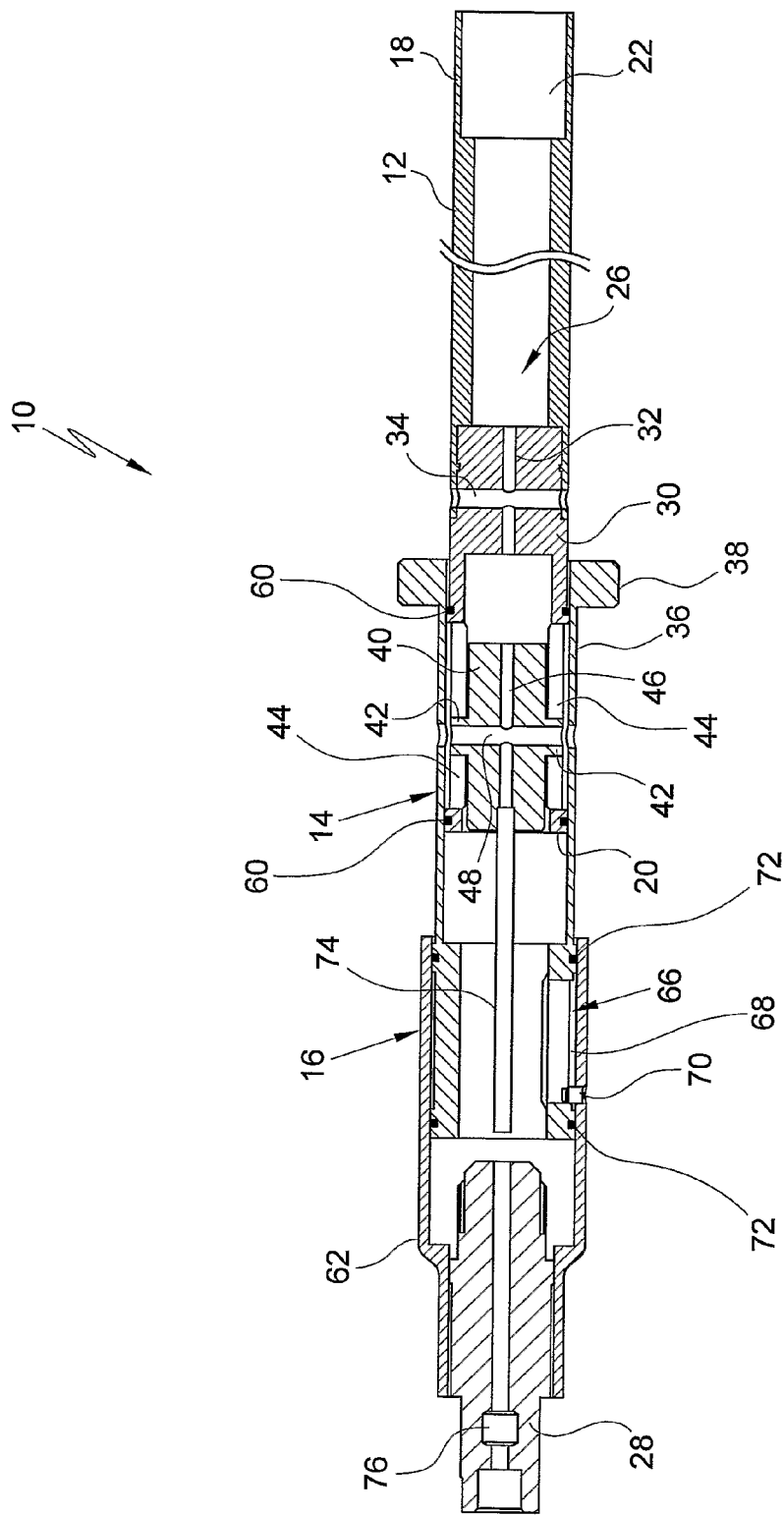
FIG. 5 shows a cross-sectional side view of the catheter handle in the second position.

To achieve this flexibility, the sleeve 62 is displaced from the position shown in FIGS. 1, 2 and 4 of the drawings to the position shown in FIGS. 3 and 5 of the drawings. When this occurs, the electrode sheath 50 moves from the position shown in FIG. 7A of the drawings to the position shown in FIG. 7B of the drawings. This allows greater flexibility of that portion of the electrode sheath 50, as shown by the dotted lines in FIG. 7B of the drawings, no longer supported by the steering shaft 54.

It will be appreciated that, with this configuration, the proximal electrode 80 (in FIG. 7B of the drawings) can be urged into tissue contact by pressure on the electrode sheath 50 being applied via the handle 10 and causing cranking of the part of the electrode sheath 50 not supported by the steering shaft 54. Pressure can then be applied proximally of that proximal electrode 80 to urge at least that electrode 80 and, possibly, any electrodes distally of that electrode 80, into more intimate tissue contact overcoming surface irregularities at the site. For difficult to access locations, the greater flexibility of the unsupported part of the electrode sheath 50 may make it easier to access such locations.

Figure 6:
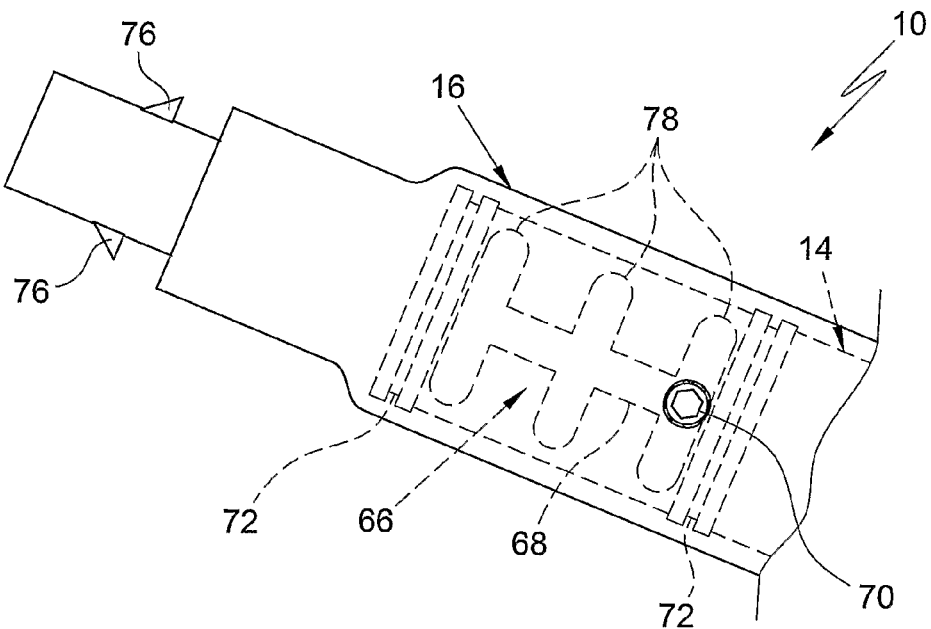
FIG. 6 shows a schematic plan view of a part of another version of a catheter handle.

In addition, in the case of the embodiment shown in FIG. 6 of the drawings, rotation of the sleeve 62 relative to the steering control mechanism 14 of the handle 10 will also allow the free, unsupported part of the electrode sheath 50 to scribe a predetermined arc allowing for the formation of longer lesions and allowing for finer positioning of the electrodes 80 relative to the site.

Figure 8:
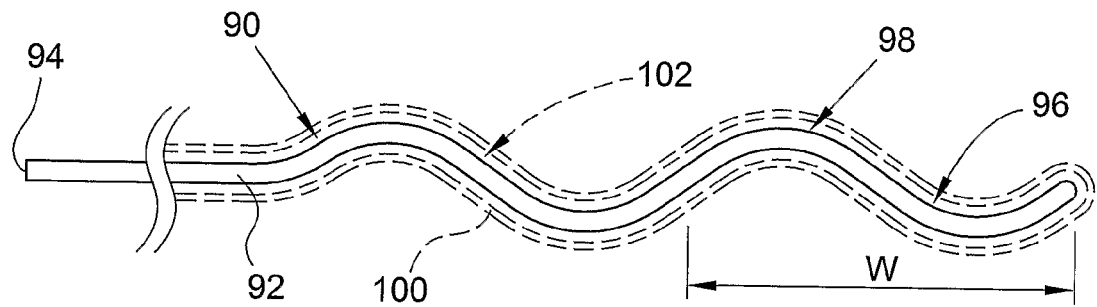
FIG. 8 shows a schematic representation of a distal part of a catheter stylet, in accordance with yet a further embodiment of the invention.

Referring to FIG. 8 of the drawings, a catheter stylet is illustrated and designated generally by the reference numeral 90. The stylet 90 has an elongate element 92 of a superlastic alloy such as nitinol. The elongate element 92 has a proximal end 94 and a distal end region 96. The distal end region 96 of the elongate element 92 carries a plurality of axially spaced contact-enhancing regions in the form of a series of undulations 98. The undulations 98 have a wavelength "w" approximately the same as a center-to-center distance between adjacent electrodes of an overlying electrode sheath 100 in a lumen 102 of which the stylet 90 is received.

Thus, in use, the stylet 90 is received in the lumen 102 of the electrode sheath 100 of the catheter and by moving the stylet 90 axially relative to the electrode sheath 100, a part of the stylet 90 is brought into register with the overlying electrode to improve electrode-tissue contact at the site being treated. For example, a "trough" of the stylet 90 may underlie the electrode. By displacing the stylet 90 axially relative to the electrode sheath 100, a "peak" of the undulations may be brought into register with the overlying electrode to improve electrode-tissue contact.

Figure 9:
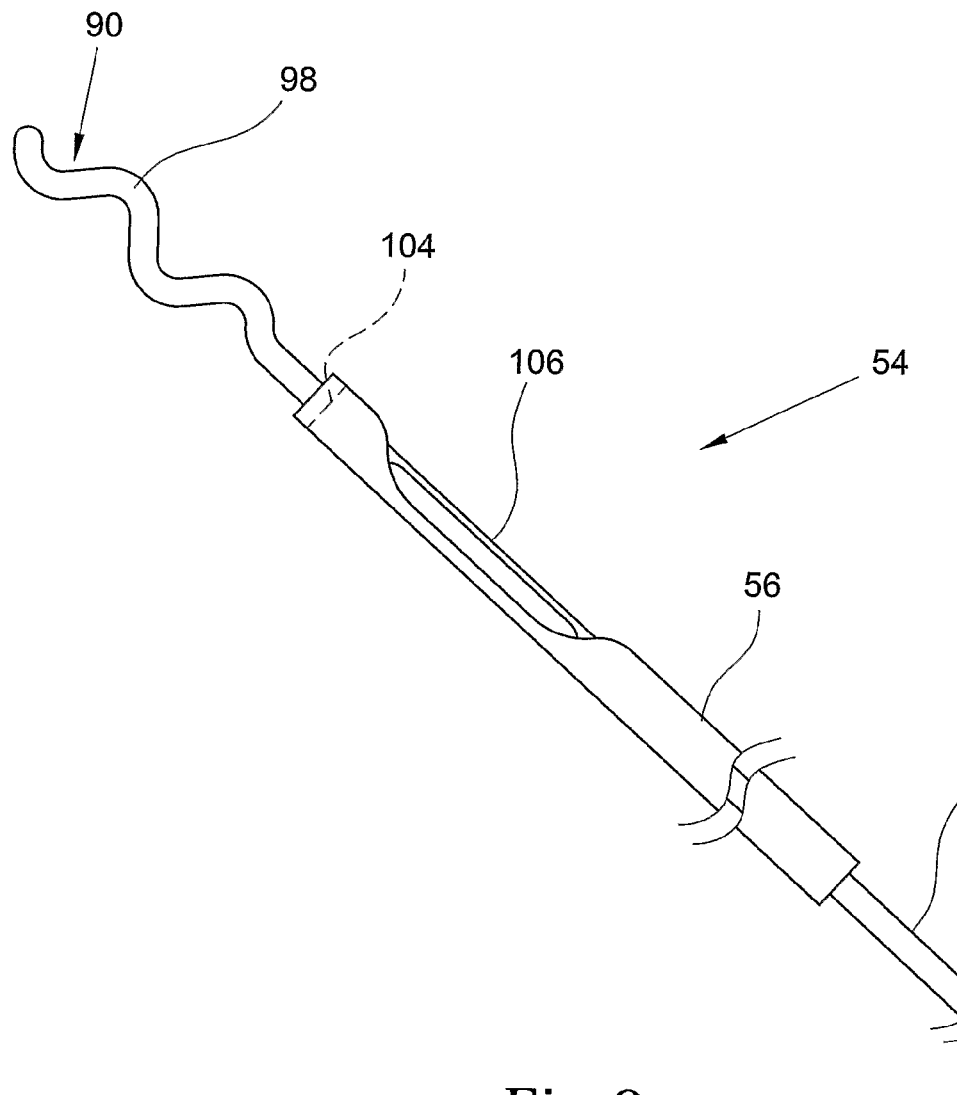
FIG. 9 shows a schematic representation of the catheter stylet of FIG. 8 implemented as a part of a steering shaft of the catheter assembly.

The stylet 90 can be implemented as part of the steering shaft 54 of the catheter 24 of the embodiment described above. Hence, as illustrated in FIG. 9 of the drawings, a distal part of the actuator 58 of the steering shaft, distally of an attachment point 104 of the actuator 58 to the tubular member 56, carries the series of undulations 98.

With this configuration of steering shaft 54, a "peak" of one of the undulations 98 can be brought into register with one of the electrodes 80 by relative axial displacement of the steering control mechanism 14 relative to the electrode sheath carrier 16. In this way, electrode-tissue contact can be enhanced to improve the quality of the lesion formed by overcoming surface irregularities at the site being treated. Electrode-tissue contact may further be improved by rotating the catheter 24.

It will be appreciated that each electrode has a length of 10 mm or less so that it is only necessary to displace the electrode sheath 50 by a few millimeters relative to the steering shaft 54 to bring a desired part of one of the undulations into register with the electrode 80.

Hence, it is an advantage of the invention that a catheter handle 10 is provided that facilitates steering of a catheter into a desired position. Greater flexibility of the electrode sheath 50 is able to be obtained, which, the Applicant believes, may result in improved electrode-tissue contact, accessibility to awkwardly located sites and may also allow for finer positioning of the electrodes 80 at the site to be treated. With this ability to obtain finer positioning of the electrodes 80, more accurate control of lesion formations should be possible. Also, the provision of the contact-enhancing regions allow for improved electrode-tissue contact to be obtained.

Another advantage of the invention is the modular nature of the handle 10. A steering shaft 54 is releasably attachable to the handle 10 and an electrode sheath is releasably attachable to the electrode sheath carrier 16. Not only does this allow certain of the parts, for example, the handle 10 and the steering shaft 54 to be reused, but it also improves the versatility of the system. It will be appreciated that, if necessary, the electrode sheath could be left in situ in a patient's body. The handle 10 and steering shaft 54 could be removed and replaced by another handle carrying a different steering shaft or a different stylet, depending on requirements.

It will be appreciated by persons skilled in the art that numerous variations and/or modifications may be made to the invention as shown in the specific embodiments without departing from the spirit or scope of the invention as broadly described. The present embodiments are, therefore, to be considered in all respects as illustrative and not restrictive.

The invention claimed is:

1. A catheter assembly, including:
a handle body;
a steering control mechanism displaceably carried on the handle body;
an electrode sheath carrier carried on a distal end of the handle body, the electrode sheath carrier being configured for releasable attachment of an electrode sheath to the handle body, and the electrode sheath carrier being axially displaceable between an operational proximal-most position and an operational distal-most position of the electrode sheath carrier relative to the steering control mechanism throughout use of the catheter assembly in the body of a patient to effect axial displacement of the electrode sheath relative to a steering shaft when both a proximal end of the steering shaft and the electrode sheath are attached to the handle body; and
an electrode sheath carried by the electrode sheath carrier, the electrode sheath including electrodes in continuous electrical connection with the catheter handle during the axial displacement of the electrode sheath carrier between the operational proximal-most position and the operational distal-most position of the electrode sheath carrier relative to the steering control mechanism.

2. The catheter assembly of claim 1, wherein the handle body is an elongate tubular member having a proximal end and a distal end, an electrical connector being arranged at, or adjacent, the proximal end of the handle body.

3. The catheter assembly of claim 1, wherein the steering control mechanism comprises a displaceable unit carried on the handle body.

4. The catheter assembly of claim 3, wherein the displaceable unit comprises a cylindrical element fast with a slider received within the handle body.

5. The catheter assembly of claim 4, wherein, to facilitate displacement of the steering control mechanism relative to the handle body, the steering control mechanism carries a manipulating element.

6. The catheter assembly of claim 5, wherein the manipulating element is a flange extending radially outwardly from the cylindrical element of the steering control mechanism.

7. The catheter assembly of claim 4, wherein the handle body and the slider include complementary guide formations for guiding displacement of the steering control mechanism relative to the handle body.

8. The catheter assembly of claim 7, wherein the complementary guide formations include at least one guide formation defined by the handle body with the slider defining at least one guide element received in the guide formation.

9. The catheter assembly of claim 4, wherein the electrode sheath carrier comprises a sleeve that cooperates with the cylindrical element of the steering control mechanism.

10. The catheter assembly of claim 9, wherein the sleeve carries an electrode connector for electrical connection to at least one of the electrodes of the electrode sheath connectable to the electrode sheath carrier.

11. The catheter assembly of claim 10, wherein the electrode connector carries a retaining formation for retaining the electrode sheath relative to the sleeve.

12. The catheter assembly of claim 9, wherein the sleeve and the steering control mechanism include complementary cooperating formations for controlling displacement of the sleeve relative to the cylindrical element of the steering control mechanism.

13. The catheter assembly of claim 1, wherein at least one of the handle body and the steering control mechanism includes anchoring formations for anchoring the steering shaft to the catheter handle.

14. The catheter assembly of claim 13, wherein the handle body includes the anchoring formations, and at least one of the anchoring formations of the handle body comprises a boss arranged within the handle body.

15. The catheter assembly of claim 1, wherein the electrode sheath has a proximal end attached to the electrode sheath carrier, and a distal end of the electrode sheath extends beyond a distal end of the steering shaft when the electrode sheath carrier is axially displaced in a distal direction relative to the steering control mechanism and the handle body such that a distal portion of the electrode sheath is unsupported by the steering shaft.

16. A catheter assembly, including:
a catheter handle having a handle body;
a steering control mechanism displaceably arranged relative to the handle body;
a steering shaft connected at least to the steering control mechanism;
an electrode sheath carrier carried on a distal end of the handle body, the electrode sheath carrier being configured for repeated releasable attachment and detachment of an electrode sheath thereto, the electrode sheath carrier being axially displaceably arranged relative to the steering control mechanism and the handle body so as to effect axial displacement of the electrode sheath relative to the steering shaft when both a proximal end of the steering shaft and the electrode sheath are attached to the handle body; and
an electrode sheath carried by the electrode sheath carrier, the electrode sheath including electrodes in continuous electrical connection with the catheter handle during axial displacement of the electrode sheath carrier relative to the steering control mechanism and the handle body to effect axial displacement of the electrode sheath relative to the steering shaft.

17. The catheter assembly of claim 16, wherein the steering shaft is releasably connected at least to the steering control mechanism.

18. The catheter assembly of claim 16, wherein the steering shaft is releasably connected both to the steering control mechanism and to the handle body so that relative displacement between the steering control mechanism and the handle body effects steering of a distal region of the steering shaft and, consequently, the electrode sheath of the catheter received over the steering shaft.

19. The catheter assembly of claim 18, wherein the steering shaft includes a tubular member having a bend-enhancing region, an actuator being slidably received in the tubular member, the actuator and the tubular member being attached to each other at an attachment point located distally of the bend-enhancing region of the tubular member, a proximal end of one of the tubular member and the actuator being connected to the steering control mechanism and a proximal end of the other of the tubular member and the actuator being connected to the handle body.

20. The catheter assembly of claim 19, wherein a distal region of the steering shaft includes a plurality of contact-enhancing regions for urging at least one of the electrodes into contact with tissue at a site being treated by appropriate manipulation of the steering shaft relative to the electrode sheath, the electrodes of the electrode sheath comprising a plurality of spaced electrodes carried by the electrode sheath.

21. The catheter assembly of claim 20, wherein the contact-enhancing regions of the steering shaft are arranged distally of the attachment point of the actuator and the tubular member.

22. The catheter assembly of claim 21, wherein the contact-enhancing regions form part of a distal region of the actuator of the steering shaft.

23. The catheter assembly of claim 16, wherein the electrode sheath carrier is displaceably carried relative to the steering control mechanism.

24. The catheter assembly of claim 23, wherein the electrode sheath carrier is displaceably carried on the steering control mechanism.

25. The catheter assembly of claim 24, wherein the electrode sheath carrier and the steering control mechanism are relatively displaceable in an axial direction and rotationally with respect to each other.

26. The catheter assembly of claim 16, wherein the distal end of the electrode sheath extends beyond a distal end of the steering shaft when the electrode sheath carrier is axially displaced in a distal direction relative to the steering control mechanism and the handle body such that a distal portion of the electrode sheath is unsupported by the steering shaft.

27. A method of controlling operation of a catheter, the method including:
axially displacing an electrode sheath relative to a handle body and a steering shaft, the electrode sheath carried by an electrode sheath carrier, the steering shaft received in a lumen of the electrode sheath, the steering shaft being connected at least to a steering control mechanism, so that a distal portion of the electrode sheath is unsupported by a distal end of the steering shaft; and
allowing flexing of the unsupported distal portion of the electrode sheath relative to the distal end of the steering shaft in a manner to form a flexed part of the electrode sheath, wherein the electrode sheath carrier is carried on a distal end of the handle body, the electrode sheath carrier being configured for releasable attachment of the electrode sheath to the handle body, the electrode sheath carrier being displaceably arranged between an operational proximal-most position and an operational distal-most position of the electrode sheath carrier relative to the steering control mechanism to effect axial displacement of the electrode sheath relative to the steering shaft when both a proximal end of the steering shaft and the electrode sheath are attached to the handle body, wherein the electrode sheath carrier is configured to provide continuous electrical connection to electrodes of the electrode sheath while the electrode sheath carrier is displaced between the operational proximal-most position to the operational distal-most position.

28. The method of claim 27, further including rotating the electrode sheath relative to the steering shaft to effect rotation of the flexed part of the electrode sheath through a predetermined arc.

* * * * *